United States Patent [19]
Gluck

[11] Patent Number: 5,409,697
[45] Date of Patent: Apr. 25, 1995

[54] BIOCIDAL COMPOSITION

[75] Inventor: Bruno A. Gluck, Dee Why, Australia

[73] Assignee: Novapharm Research Pty. Ltd., Australia

[21] Appl. No.: 837,687

[22] Filed: Feb. 19, 1992

Related U.S. Application Data

[63] Continuation of Ser. No. 455,418, Jan. 2, 1990, abandoned.

[30] Foreign Application Priority Data

Jul. 1, 1987 [AU] Australia ................. PI2820

[51] Int. Cl.⁶ ............. A61K 33/18; A01N 59/12
[52] U.S. Cl. ................. 424/78.25; 424/667; 424/668; 424/669
[58] Field of Search ........... 424/80, 130, 667, 672, 424/78.36, 668, 669, 78.25

[56] References Cited

U.S. PATENT DOCUMENTS

| | | | |
|---|---|---|---|
| 3,898,326 | 8/1975 | Cantor et al. | 424/667 |
| 4,017,407 | 4/1977 | Cantor et al. | 424/667 |
| 4,031,209 | 6/1977 | Kalzoroski | 424/150 |
| 4,130,640 | 12/1978 | Chazan et al. | 424/150 |
| 4,151,275 | 4/1979 | Cantor et al. | 424/150 |
| 4,320,114 | 3/1982 | Denzinger et al. | 424/78.25 |

FOREIGN PATENT DOCUMENTS

| | | |
|---|---|---|
| 8770875 | 6/1977 | Australia . |
| 3491878 | 12/1981 | Australia . |
| 2464384 | 8/1987 | Australia . |
| 1050382 | 8/1979 | Canada . |
| 6548 | 1/1980 | European Pat. Off. . |
| 1580596 | 12/1980 | United Kingdom . |
| 2084875 | 4/1982 | United Kingdom . |

OTHER PUBLICATIONS

Schenck et al., "Structure of Polyvinylpyrrolidone-Iodine (Providone-Iodine")", Journal of Pharmaceutical Sciences, vol. 68, No. 12, Dec. 1979, pp. 1505–1509.

*Primary Examiner*—Gollamudi S. Kishore
*Assistant Examiner*—Peter F. Kulkosky
*Attorney, Agent, or Firm*—Cushman Darby & Cushman

[57] ABSTRACT

A stable organic iodophor composition including an iodophor wherein the ratio or organic iodine solubilizing compound to iodine is less than 5:1 by weight, and a process for the production of an iodophor composition which process includes dissolving an organic iodine solubilizing compound and iodine or an iodine liberating substance in water in amounts such that the ratio of iodine liberating substance to iodine is less that 5:1 by weight and optionally adjusting the pH. adding an oxidizing agent and readjusting the pH following oxidation.

2 Claims, 1 Drawing Sheet

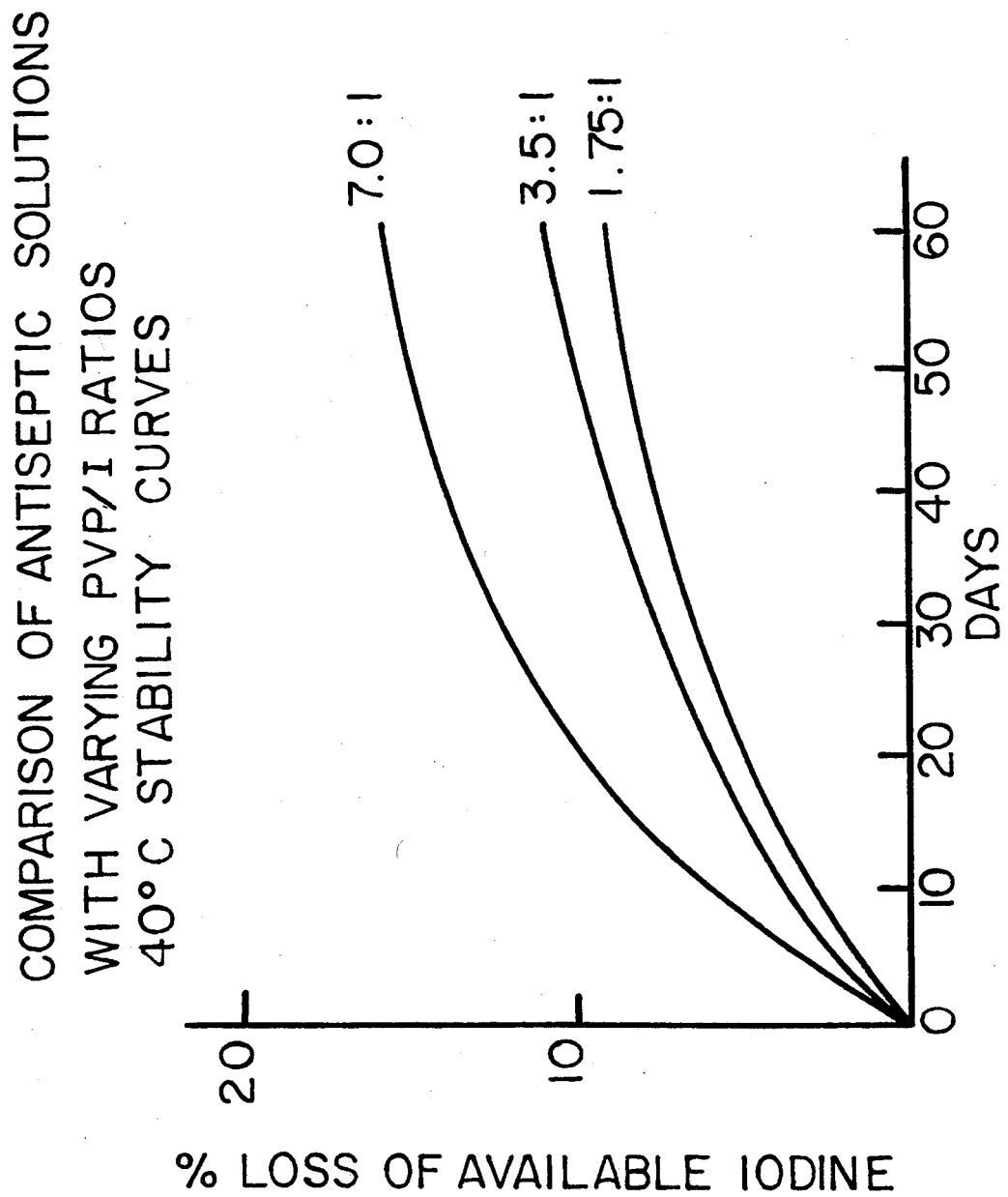

BIOCIDAL COMPOSITION

This is a continuation of application Ser. No. 07/455,418, filed on Jan. 2, 1990, now abandoned.

TECHNICAL FIELD

The present invention relates to iodophor germicidal compositions and more particularly to the production of low cost iodophor germicidal compositions of improved stability by virtue of their unusually low PVP:$I_2$ ratios.

BACKGROUND ART

There has been in the past a continuing effort to develop a germicidal composition which is stable and cheap to manufacture.

The advantages of iodine condensed with a carrier, known as an iodophor and resulting in complex formation, over previously used iodine preparations such as Tincture of iodine and Lugol's solution are well documented.

The art is rich in attempts to efficiently produce an iodophor complex which is both cheap to prepare and stable over a period of time.

It was previously believed that such compositions needed a high PVP:$I_2$ ratio for stability.

For example in U.S. Pat. No. 3,028,300 iodine and iodide are combined directly with polyvinylpyrrolidone, hereinafter known as PVP, in the dry state. U.S. Pat. No. 3,028,300 teaches that the PVP to iodine ratio must be at least 3:1 and the iodide to iodine ratio greater than 0.5. The disadvantage with this process is that the stability of the complex form decreases with decreasing proportions of PVP as shown in the tables illustrating the invention. No complex can be formed when the PVP to iodine is less than 3:1.

The process of U.S. Pat. No. 4,113,857 also uses for the iodine complex formation, oxidation of an iodine containing substance by an oxidising medium but with the following significant important difference to the present invention, namely the use of an excess of oxidising agent such as hydrogen peroxide or potassium iodate which leaves the final product free of iodide, claimed to be an essential and integral part of the invention. In contrast the present invention requires at least 10% of iodide calculated on the iodine of the complex.

U.S. Pat. No. 4,320,114 discloses a PVP-iodine complex wherein the complex is formed by combining, eg KI, PVP, and hydrogen peroxide. The pH is adjusted to between 2 and 7. The iodine is formed in situ by adding an oxidizing agent for partially converting the iodide ions into free iodine.

German Patent 27 18 385 discloses a process for forming a PVP-iodine complex by incomplete oxidation of iodide 4) and a ratio of PVP-iodine of approximately 5:1.

Spanish Patents 545 377 and 86-08317 disclose PVP-iodine complexes formed with a 10% excess of KIO$_3$. Complete oxidation of the iodide would be expected. The ratio of PVP:iodine is 10:1.

United Kingdom Patent 2 084 875 discloses a composition in dry form, to be dissolved in water shortly before use. The iodophor is formed after dissolution in water. The ratios claimed are broad. The example discloses a 2:1 weight ratio for the PVP:KI, but no or little excess iodide would be expected as the iodide and the perborate are added in approximately equimolar amounts, based on the oxidizing strength of the perborate.

U.S. Pat. Nos. 3,898,326 and 4,017,407 provide iodine by direct addition.

U.S. Pat. No. 4,130,640 discloses a germicidal composition containing a sulfated fatty alcohol and/or a sulfosuccinates of a fatty alcohol in combination with PVP-iodine or iodine/iodide.

U.S. Pat. No. 4,402,937 requires that the ratio of iodine:iodide be about 2:1. The solution is stabilized with the addition of a reducing rather than an oxidizing agent which reduces iodine to iodide.

U.S. Pat. No. 4,526,751 discloses a weight ratio of about 2:1 for PVP:interhalogen solution and about 0.5:1 for iodide:iodine.

U.S. Pat. No. 4,038,476 discloses free-flowing granules of practically uniform composition and particle size consisting of PVP and iodide by combining with uniform thorough mixing a solution and/or colloidal suspension of a substance releasing iodide ions in a first solvent. The mixture as well as a solution and/or colloidal suspension and/or suspension of PVP in a second solvent or solvent mixture which possesses surface tension different from that of the first solvent or solvent mixture and in which PVP is at least partially soluble or wettable and in which the substance releasing iodide ions contained in the first solvent or solvent mixture is insoluble or only slightly soluble.

U.S. Pat. No. 4,125,602 is directed to the preparation of iodophor granules of practically uniform particle size consisting of PVP, iodine and a substance releasing iodide ions by combining with uniform thorough mixing a solution and/or colloidal suspension of elementary iodine and a substance releasing iodide ions in a first solvent or solvent mixture as well as a solution and/or colloidal solution and/or suspension of PVP in a second solvent or solvent mixture which has a surface tension different from that of the first solvent or solvent mixture and in which PVP is at least partially soluble or wettable and in which the substance is dissolved or suspended in the first solvent or solvent mixture are insoluble or only slightly soluble and separating and drying the granules formed.

DISCLOSURE OF THE INVENTION

In accordance with one broad form of the invention there is provided a stable organic iodophor composition comprising an iodophor wherein the ratio of organic iodine solubilizing compound to iodine is less than 5:1 preferably containing between 10 and 60% by weight of an iodine liberating substance.

The organic iodine solubilizing compounds suitable for this invention can be selected from cationic surfactants, non-ionic surfactants, polymers such as PVP, and copolymers. Suitable cationic surfactants are quaternary ammonium salts. Suitable non-ionic surfactants have the general formula RO(CH$_2$CH$_2$O)$_n$OH where R is nonylphenol, a fatty acid or fatty alcohol residue and where n is an integer greater than 3. The most form of PVP is PVP K30.

Suitable iodine liberating substances include hydroiodic acid, and alkali metal iodides preferably potassium iodide.

In accordance with another broad form of the invention there is provided a process for the production of an iodophor of improved stability comprising the steps of dissolving an organic iodine solubilizing compound and an iodine liberating substance and an oxidising compound in water, adjusting the pH value for example by adding sufficient nonorganic or organic acid such as phosphoric-, sulphuric-, hydrochloric-, sulphamic- or oxalic-, citric- or lactic acid so that the pH after all the iodine has been complexed is below 7.0. The pH may be then adjusted with alkali or acid to the desired pH level preferably if PVP is the complexing substance, between 3.5–5.5 and in the case of a non-ionic below 2.5, depending on the application, and adding an oxidising agent.

Examples of suitable oxidising compounds are peroxides, such as hydrogen peroxide; iodates; and persulfates such as sodium, potassium or ammonium persulfates. It is preferred that hydrogen peroxide is used as an oxidising agent and that is used at a concentration of between 22.5% and 30%.

The invention is characterised by forming an iodophor through liberation of iodine from an iodine liberating substance by an oxidising agent in the presence of an organic iodine solubilising compound in the proportion of 5:1 or less and leaving an excess iodide. The iodophor, thus obtained, shows improved stability when the proportion of iodine to the organic iodine complex forming substance is increased, contrary to what could be expected from the PVP:I complex prepared as described in the previous art.

For example a PVP-iodine complex where the proportion of PVP to iodine is 1.75:1 is significantly more stable than the complex where the proportion is 7:1. The latter proportion is the accepted value in commercially available PVP-iodine products.

It is obvious that the qualitative improvement of the iodophor obtained by the newly invented process, offers the additional advantage of cost savings by using only one fourth of the amount of PVP used in prior art processes.

In another broad form this invention provides a method for the antiseptic and disinfecting treatment of organic and inert surfaces requiring such treatment, which method comprises treating said object with an effective amount of the composition described above, for a period of time sufficient to affect desired asepsis.

BRIEF DESCRIPTION OF DRAWING

The drawing shows loss of available iodine in aqueous solutions containing the povidone iodine concentrates at various povidone to iodine ratios.

BEST MODES FOR CARRYING OUT THE INVENTION

The following examples illustrate preferred embodiments of the invention and should not be construed as limiting thereon.

EXAMPLE 1

PVP:I ratio 1.75:1
ANTISEPTIC TINCTURE (0.1% w/v AV. IODINE)

1.75 g of PVP K30, 5 g glycerol, and 1.1 g of potassium iodide was dissolved in 100 ml of water. Phosphoric acid (0.7 ml, 85%), was then added with slow stirring, followed by 0.6 ml of 27.5% hydrogen peroxide. The solution was allowed to stand for at least 12 hours and the pH adjusted using either phosphoric acid or sodium hydroxide to approximately 4.5. Ethyl alcohol, (700 ml) was added and the volume adjusted with water, approx. 200 ml, to give a final available iodine of 0.1% w/v.

EXAMPLE 2

PVP:I ratio 1.75:1
ANTISEPTIC OINTMENT (5% w/v IODINE)

A mixture of 72.5 gm of polyethyleneglycol 400 and 17.5 gm polyethyleneglycol 4000 is heated to approximately 45 to 50 degrees C. with stirring. Heating is continued until a clear even liquid is obtained. Then 10 gm with a PVP:I ratio of 1.75:1 and an available iodine content of 5% is slowly stirred in. Stirring is continued until an even product is obtained and then allowed to cool. An even smooth easily applied to the skin antiseptic is obtained.

EXAMPLE 3

PVP:I ratio 5:1
ANTISEPTIC SOLUTION (1% w/v AV. IODINE)

50 g Polyvinylpyrrolidone K30 and 22 g of potassium iodide was dissolved in 200 ml of water. Phosphoric acid (7 ml, 85%), was added with slow stirring followed by 6 ml of 27.5% hydrogen peroxide. The solution was allowed to stand for at least 12 hours and the pH adjusted with either phosphoric acid or sodium hydroxide to approx. 4.5. Sufficient water, approx. 800 ml, was added to give a final available iodine content of 1% w/v.

EXAMPLE 4

PVP:I ratio 3:1
TEAT DIP FOR MASTITIS CONTROL (0.5% w/v AV. IODINE)

15 g of PVP K30, 50 g of glycerol and 11 g of potassium iodide was dissolved in 200 ml of water. Phosphoric acid (3.5 ml, 85%), was then added with slow stirring, followed by 3 ml of 27.5% hydrogen peroxide. The solution was allowed to stand for at least 12 hours and the pH adjusted to approximately 4.5 with either phosphoric acid or sodium hydroxide. Sufficient water, approximately 800 ml, was added to give a final available iodine content of 0.5% w/v.

EXAMPLE 5

PVP:I ratio 3:1
POVIDONE IODINE CONCENTRATE 150 g of PVP K30 and 110 g of potassium iodide was dissolved in 500 ml of water. 35 ml of 85% Phosphoric acid was then added with slow stirring followed by 30 ml of 27.5% hydrogen peroxide. The solution was allowed to stand for at least 12 hours and the pH adjusted to approx. 4.5 with either phosphoric acid or sodium hydroxide. Sufficient water, approx. 175 ml, was added to give a final available iodine content of 5.0% w/v.

The concentrate can be used as starting material for the manufacture of various antiseptic and disinfecting products for various applications and concentrations.

COMPARATIVE EXAMPLE 1

EFFECT OF OXIDIZERS ON PVP-I STABILITY

Table I shows the effect of added oxidizers in excess of theoretical quantity necessary to liberate all iodine from the iodine liberating substance on the stability of an aqueous PVP-I solution containing 1% available iodine. For all batches a PVP-I ratio of 7:1 was employed and all samples were stored at accelerated testing conditions of 55° C. The test solutions were stored in stoppered clear dark brown glass bottles. Aliquots were sampled at the intervals shown in the table and the concentration of iodine determined using the thiosulphate method.

TABLE 1

| | % AVAILABLE IODINE LOSS AT 55° C. | | |
|---|---|---|---|
| OXIDIZER | 5 DAYS | 7 DAYS | 14 DAYS |
| Control | 17.0% | 27.4% | 39.6% |
| Hydrogen peroxide | 22.8% | 36.2% | 54.3% |
| Sodium persulfate | 55.2% | 69.5% | 98.1% |
| Potassium iodate | 84.9% | 93.7% | 100% |

COMPARATIVE EXAMPLE 2

EFFECT OF INCREASING RATIO OF PVP:I ON STABILITY

Table 2 shows the effect of increasing the ratio of PVP:I. For all batches hydrogen peroxide was employed as the oxidising agent leaving an excess iodide in the product. All samples were stored at accelerated testing conditions of 55° C.

TABLE 2

| | % AVAILABLE IODINE LOSS AT 55° C. | | | |
|---|---|---|---|---|
| PVP:I | INITIAL | 1 DAY | 7 DAYS | 14 DAYS |
| 1.75:1 | 0.0 | 4.0 | 12.3 | 22.1 |
| 3.50:1 | 0.0 | 8.0 | 24.1 | 41.1 |
| 5.00:1 | 0.0 | 7.8 | 29.6 | 44.3 |
| 7.00:1 | 0.0 | 8.6 | 36.2 | 54.3 |

COMPARATIVE EXAMPLE 3

The results of these tests show that the ratio of the complexing substance to iodine has no influence on the microbiocidal effectiveness of the iodine complex, provided the available iodine remains the same. Comparison of antimicrobial activity of PVP-I complex of a high and low PVP:I ratio was carried out by the Minimum Inhibitory Concentration (M.I.C.) method

TABLE 3

| TEST ORGANISMS | Culture Count (cfu/ml) |
|---|---|
| *Escherichia coli* | $6.4 \times 10^9$ |
| *Staphylococcus aureus* | $6.3 \times 10^9$ |
| *Pseudomonas aeruginosa* | $3.0 \times 10^9$ |
| *Proteus vulgaris* | $6.0 \times 10^9$ |

$20\mu$ of the above cultures was inoculated into the test solution. The test solutions were prepared by making doubling serial dilutions using Difco AOAC medium.

TABLE 4

| | RESULT: | | | |
|---|---|---|---|---|
| | Dilution | | | |
| Culture | 1/25 | 1/50 | 1/100 | 1/200 |
| PVP:I = 7:1 | | | | |
| *E. coli* | − | − | − | + |
| *S. aureus* | − | − | − | − |
| *Ps. aeruginosa* | − | − | − | + |
| *P. vulgaris* | − | − | − | + |
| Controls satisfactory. | | | | |
| PVP:I = 1.75:1 | | | | |
| *E. coli* | − | − | − | + |
| *S. aureus* | − | − | − | − |
| *Ps. aeruginosa* | − | − | − | + |
| *P. vulgaris* | − | − | − | + |
| Controls satisfactory. | | | | |

The foregoing describes only some embodiments of the present invention and modifications, obvious to those skilled in the art, can be made thereto without departing from the scope of the present invention.

I claim:

1. An organic iodophor complex of improved stability in an aqueous solution comprising polyvinylpyrrolidone:iodine (PVP:I) as an iodophor and hydroiodic acid or an alkali metal iodide;

wherein the ratio of PVP to iodine is from 1.75:1 to 3:1 by weight;

wherein the complex has a pH value of less than 7; and wherein the hydroiodic acid or alkali metal iodide is "present in an amount of between 10 and 60 per cent" by weight of the complex.

2. A method for the antiseptic and disinfecting treatment of organic and inert surfaces requiring such treatment, which method comprises treating said surface with an effective amount of the complex of claim 1 for a period of time sufficient to effect desired asepsis.

* * * * *